US006401537B1

(12) United States Patent
Gigliotti, Jr. et al.

(10) Patent No.: US 6,401,537 B1
(45) Date of Patent: Jun. 11, 2002

(54) TITANIUM-BASED ALLOYS HAVING IMPROVED INSPECTION CHARACTERISTICS FOR ULTRASONIC EXAMINATION, AND RELATED PROCESSES

(75) Inventors: Michael Francis Xavier Gigliotti, Jr., Scotia; Robert Snee Gilmore, Burnt Hills; John Broddus Deaton, Jr., Niskayuna; John Alan Sutliff, Burnt Hills, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/346,914

(22) Filed: Jul. 2, 1999

(51) Int. Cl.$^7$ .......................... G01N 29/04; C22C 14/00
(52) U.S. Cl. ............................ 73/598; 73/600; 420/417
(58) Field of Search .......................... 73/642, 622, 644, 73/626, 627, 628, 625, 620, 618, 641, 637, 602; 420/417; 148/669, 670, 671, 421

(56) References Cited

U.S. PATENT DOCUMENTS

| | | | |
|---|---|---|---|
| 4,539,848 A | * 9/1985 | Takafuji et al. | 73/602 |
| 4,719,583 A | * 1/1988 | Takafuji et al. | 73/760 |
| 4,854,977 A | 8/1989 | Alberitiere et al. | 148/417 |
| 5,026,520 A | * 6/1991 | Bhowal et al. | 148/133 |
| 5,277,718 A | * 1/1994 | Paxson et al. | 148/670 |
| 5,406,850 A | * 4/1995 | Bouchard et al. | 73/620 |
| 5,471,879 A | 12/1995 | Vinot et al. | 73/622 |
| 5,533,401 A | 7/1996 | Gilmore | 73/622 |

OTHER PUBLICATIONS

"Effects of Ti–6A1–4V Alloy Metallurgical Structures on Ultrasonic Response Characteristics," FR Billman; FF Rudolph; Titanium Science and Technology; Proceedings of the Second Inter. Conf—The Metallurgical Society of AIME; May 2–5, 1972; pp. 693–705.

"The Influence of Microstructure on Ultrasonic Response in a Titanium Alloy Forging," B. Ginty; P. Hallam; C. Hammond; G. Jackson; C. Robb; Titanium '80 Science & Technology; Proceedings of the Fourth Inter. Conf. on Titanium; May 19–22, 1980; pp. 2095–2103.

"High Noise Levels During the Ultrasonic Testing of Titanium Alloys," RK Granville; JL Taylor; British Journal of NDT; May 1985; pp. 156–158.

"An Experimental Investigation of Ultrasonic 'Grain Noise'in Titanium–6AL–4V," Sam Foister; SG McKenzie; RC Chivers; report Rolls–Royce plc, Derby, DE24 8BJ, U.K., pp. 1–7.

"Formation of Submicrocrystalline Structure in the Titanium Alloy VT8 and its Influence on Mechanical Properties," GA Salishchev; OR Valiakhmetov; RM Galeyev; Institute of Metals Superplasticity Problems, Russian Academy of Sciences; 0022–2461 1993 Chapman & Hall; pp. 2898–2902.

\* cited by examiner

*Primary Examiner*—Helen Kwok
(74) *Attorney, Agent, or Firm*—Robert P. Santandrea; Noreen C. Johnson

(57) ABSTRACT

A method for inspecting a titanium-based alloy that comprises alpha phase grains to detect flaws in the titanium-based alloy, the titanium-based alloy comprises an alpha phase that is provided by thermomechanically processing the alloy to provide a microstructure which comprises the alpha phase that defines an average grain size and a crystallographic orientation of the grains of the alpha phase that is highly randomized. The method comprises ultrasonically inspecting the titanium-based alloy using an ultrasonic beam, the ultrasonic beam comprising a cross-sectional area that is less than the average grain size of the alpha phase in the titanium-based alloy; and determining flaws based on the step of ultrasonic inspecting.

33 Claims, 7 Drawing Sheets

TITANIUM-BASED ALLOYS HAVING IMPROVED INSPECTION CHARACTERISTICS FOR ULTRASONIC EXAMINATION, AND RELATED PROCESSES

BACKGROUND OF THE INVENTION

This invention relates generally to titanium-based alloys utilized in high-performance applications. More specifically, it relates to titanium-based alloys which are inspected for defects by employing ultrasonic techniques.

Titanium-based alloys are very useful materials because of their attractive combination of high strength and relatively low weight, at temperatures up to about 550° C. They are therefore the material of choice for high performance components, such as compressor discs for aircraft propulsion systems. A wide range of alloys are available, each conferring a particular combination of characteristics to the component. In terms of end use applications, titanium alloys have replaced steel in the 200° C.–500° C. use temperature, and can often replace cobalt- and nickel-base alloys at higher temperatures.

The microstructure of titanium alloys has been the object of extensive research. It's well understood that many important titanium alloys consist of at least two phases: an alpha ($\alpha$) phase which has a hexagonal close packed crystal structure, and a beta ($\beta$) phase which is body-centered cubic. Transformation from $\alpha$ to $\beta$ (in pure titanium) is known to occur at a temperature of about 880° C. Alloying elements are frequently used to alter the $\alpha$-$\beta$ transformation temperature. For example, aluminum, tin, and zirconium are common $\alpha$—stabilizing elements, while vanadium, molybdenum, and tantalum are common $\beta$—stabilizing elements. Thermomechanical processing techniques for converting a cast billet of titanium into a finished article are generally well-known in the art.

Titanium alloys used for aerospace components must be of the highest quality. It is therefore necessary to inspect the alloy during various stages, such as the billet stage. As described in U.S. Pat. No. 5,533,401 (R. Gilmore), titanium billets are often formed from cylindrical ingots having a diameter of 30–36 inches, and a weight in the range of 7000–10,000 pounds. The ingots can be forged into a series of cylindrical billets, which can vary from 6 to 15 inches in diameter. Individual billet segments often are 10–20 feet in length.

Various types of nondestructive testing are available to determine the quality of the alloy, i.e., the type and amount of flaws within its microstructure. Examples of test methods include neutron imaging, electron imaging, and ultrasonic examination. Ultrasonic testing is one exemplary test method, in which ultrasonic tests are performed by introducing beams of high frequency sound waves into the material under investigation. Test signals indicate amplitudes and arrival times of transmitted, reflected, and refracted waves. The signals can also detect various interfaces and internal discontinuities within the object, e.g., grain boundaries, voids, cracks; and inclusions of foreign material, such as hard alpha inclusions. An ultrasonic transducer usually serves as both a generator of the ultrasonic beam and a detector of the attenuated sound waves which are produced from surfaces and interior discontinuities within the object. These sound waves are converted into electrical signal oscillations for inspection.

One particular type of ultrasonic technique is referred to as immersion testing, where the object being examined is submerged in a tank of liquid, and the sound beam from an ultrasonic transducer interrogates the test object. While many variations and additional accouterments are commercially available, the same general principles of ultrasonics are employed.

In the referenced patent of R. Gilmore, a multi-zone ultrasonic apparatus is described. Such a device is very useful for inspecting the entire volume of an object, such as a titanium billet. The device usually employs a plurality of ultrasonic transducers having focal zones at increasing depths, with adjacent focal zones overlapping each other. Additional features include a system for collecting data so that the billet can be examined as a series of C-scan images generated from each of the transducer signals.

The presence of "microstructural noise" in objects such as those made from titanium alloys can sometimes limit the ability of the ultrasonic apparatus to detect flaws—even when using a multi-zone ultrasonic apparatus. This situation is described by S. Foister et al in "An Experimental Investigation of Ultrasonic 'Grain Noise' in Titanium-6AI-4V"; Review of Progress in Quantitative Nondestructive Evaluation; Plenum Press, Vol. 15B, pp. 1479–1486 (1996). While ultrasonic pulses are desirably reflected by bona fide flaws in the material, they can also reflect off benign features, such as grain boundaries.

Although the grain boundary reflections (i.e., "grain noise") are usually characterized by a distinct amplitude, at least two problems arise from the presence of intrinsic microstructural noise. First, the smallest flaw signals cannot be observed because they are masked by the grain noise, thereby limiting the detection capability of the ultrasonic scan. Second, the largest noise signals may be mistaken for flaws, resulting in numerous "false calls", which in turn can lead to the rejection of good material.

It should thus be apparent that further improvements in the ultrasonic detection of flaws in titanium-based alloys would be welcome in the art. Moreover, the discovery of titanium-based materials which intrinsically exhibit a high level of ultrasonic "inspectability" would also represent a very significant advance in technology. Such materials should be amenable to a variety of different types of ultrasonic inspection techniques. The materials should also continue to exhibit, in their final form for use, substantially all of the properties sought after in titanium alloys, such as tensile strength, corrosion resistance, and fatigue crack growth resistance.

SUMMARY OF THE INVENTION

As disclosed in PCT Application WO 98/17836, several methods are disclosed for forming titanium, as embodied by the invention. For example, the titanium material that is subject to the inspection, as embodied by the invention, can be formed from nay one of the processes set forth in the Examples of the PCT Application WO 98/17836. Further, the titanium material that is subject to the inspection, as embodied by the invention, can be formed by other processes. For example, A method for preparing a titanium alloy article in which the titanium comprises a substantially controlled homogeneous fine grain microstructure. The method comprises the steps of: providing a titanium alloy article having an initial grain size (do); selecting a final homogeneous fine grain size (dk) to be achieved in the titanium alloy article; plotting a curve of the relationship between a recrystallized grain size (d) for the titanium alloy on the y-axis versus a strain temperature (T) for the alloy on the x-axis, between a range of 400° C. and a temperature of complete polymorphous transformation (Tcpt), in accordance with the relationship d=f(T); locating an area (T*) on the strain temperature axis to divide the temperature axis into two zones comprising a first zone 400° C. to T*, and a second zone T* to Tcpt, where the T* is located by first calculating a corresponding recrystallization grain size (d*) on the y-axis, where d* is logarithmically related to the initial grain size do; further locating, on the curve, the final grain size (dk) on the y-axis and then a corresponding strain temperature (Tk) on the x-axis; determining the heating and deforming step or steps to process the article based on Tk, where for Tcpt>Tk>T*, and there is at least one heat and deforming step to obtain the final grain size dk, where Tk<T*, there are at least two heat and deforming steps where each heat and deforming step occurs for a sufficient amount of time to reduce the grain size of the titanium alloy article until the final grain size dk is obtained; heating and deforming the titanium alloy article in accordance with the determined number of heat and deforming steps to achieve (dk), where each heat and deforming step has at least one heating and deforming step and one cooling step, where the heat and deforming step occurs for a sufficient period of time to reduce the grain size of the titanium alloy article, and where the deformation of the titanium alloy article is in a substantially controlled manner during each heat and deforming step at a rate of strain to achieve the desired grain size of the heat and deforming step, where the true strain during the deformation is greater than or equal to about 0.6 for each heat and deforming step, and where the subsequent cooling is controlled at a temperature below the heat and deforming step temperature at a cooling rate for substantially maintaining the reduced grain size obtained during the heat and deforming step; and repeating the step of heating and deforming the titanium alloy article in accordance with the determined number of heat and deforming steps to achieve homogeneous grain size(dk), until a final substantially controlled homogeneous grain size dk is obtained in the article having substantially homogeneous mechanical properties.

Another method for making a substantially controlled homogeneous fine grain microstructure in a titanium alloy article, as embodied by the invention, comprises the steps of: heating and deforming titanium material at a predetermined heat and deforming step temperature that is at or below a temperature of complete polymorphous transformation where the titanium alloy article has sufficient ductility and a starting grain size, in which the heat and deforming steps comprise at least one heat and deforming step and at least one cooling step. The heat and deforming steps is conducted for a sufficient amount of time to reduce the grain size from a starting grain size to a reduced grain size at the end of the heat and deforming step. The deforming of the titanium occurs in a controlled manner at a rate of strain that is able to achieve a desired grain size, where a true strain during the deformation is greater than or equal to about 0.6 for each heat and deforming step and where the cooling step is performed after the heat and deforming step at a temperature below the heat and deforming step temperature, in a controlled manner at a cooling rate to substantially maintain the reduced grain size obtained during the heat and deforming step. The method also includes continuing to heat and deform then cool the titanium alloy article, in which the heating occurs at lower heat and deforming step temperatures than the previous heat and deforming step temperature, so a reduction of grain size is achieved in subsequent heat and deforming steps until a final controlled grain size with controlled mechanical properties is obtained in the titanium alloy article.

DETAILED DESCRIPTION OF THE INVENTION

Figure 1:
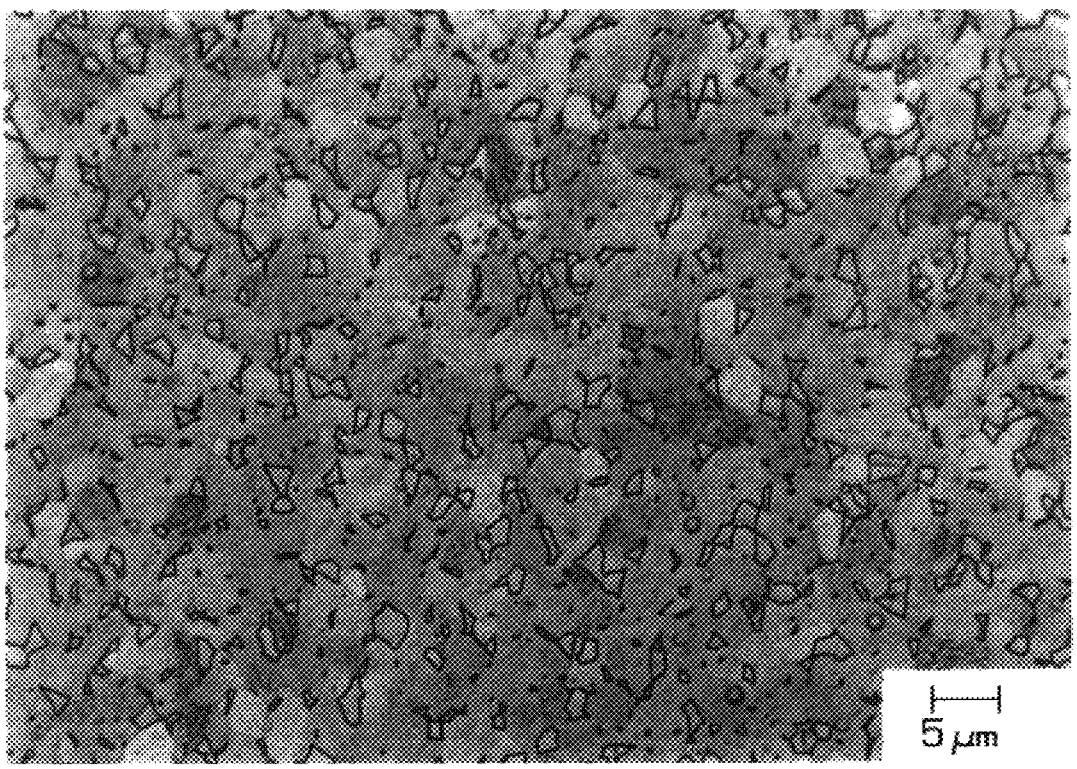
FIG. 1 is a photomicrograph of a titanium-based alloy for the present invention, having a characteristic microstructure.

The alloy content for the titanium-based materials, as embodied by the invention, may vary. In general, titanium materials, as embodied by the invention, typically comprise two categories: an all—$\alpha$ structure, or a mixed $\alpha$-$\beta$ structure, with the latter being most common.

Various elements are used to stabilize the titanium structure in a particular phase, by altering the $\alpha$-$\beta$ transformation temperature. Aluminum, tin, and zirconium are the common $\alpha$—stabilizing elements, along with interstitial elements such as oxygen, nitrogen, and carbon. Aluminum is often the an alloying element. Vanadium, molybdenum, tantalum, and niobium are common $\beta$—stabilizing elements. $\beta$—eutectoid elements can also be used as $\beta$—stabilizers. Examples are manganese, iron, chromium, cobalt, nickel, and copper.

Titanium alloys containing aluminum and, optionally, vanadium, that are within the scope of the invention typically comprise at least one element selected from tin, zirconium, and molybdenum. The amount of each alloying element will be determined in large part by the property requirements for the alloy. Usually, each alloying element is employed at a level of about 1 wt. % to about 10 wt. %, and for example, from about 2 wt. % to about 7 wt. %, based on the total weight of the alloy.

Specific, non-limiting examples of titanium alloys suitable for this invention are the following (numbers represent the approximate weight percent of the alloy): Ti-6 Al-4 V; Ti-6 Al-2 Sn-4 Zr-2 Mo; Ti-3 Al-2.5 V; Ti-6 Al-6 V-2 Sn; Ti-1 0 V-2 Fe-3 Al; Ti-5 Al-2.5 Sn; Ti-6 Al-2 Sn-4 Zr-6 Mo. Commercial examples are: IMI™ 550 (Ti-4 Al-2 Sn-4 Mo-0.5 Si); IMI™ 829 (Ti-5.5 Al-3.5 Sn-3 Zr-1 Nb-0.2 Mo-0.3 Si); and IMI™ 834 (Ti-5.8 Al-4 Sn-3.5 Zr-0.7 Nb-0.5 Mo-0.35 Si-0.06 C); General Electric Company's Ti-17 (Ti-5 Al-2 Sn-2 Zr-4 Cr-4 Mo); and Timet™ Ti-1100 (Ti-6 Al-2.7 Sn-4 Zr-0.4 Mo-0.45 Si). Those of skill in the art are familiar with the preparation and associated metallurgical treatments related to many of these titanium alloys.

The average grain size of the alpha phase is substantially smaller than the cross-sectional area of the beam utilized in an ultrasonic examination, as embodied by the invention. In standard terminology, the "diameter" of the beam of an ultrasonic device (some of which use "focused" beams) is defined as the diameter at which the acoustic amplitude of the device is decreased by one-half. This quantity is sometimes referred to as the "6 dB (decibel) diameter". The average grain size of the alpha phase is less than about 10% of the beam diameter. The average grain size is less than about 1% of the beam diameter. This average grain size is also typically less than about 1% of the wavelength of the carrier frequency of the sound beam.

In terms of quantities which generally correlate to the (grain size—beam diameter-relationship) set forth above, the average grain size of the alpha phase is usually less than about 50 microns, and most often, less than about 5 microns. Moreover, the alpha particles are usually euhedral, i.e., having a shape with substantially equal angles and sides, (e.g., they could be substantially spherical). The particles typically have an average surface area-to-volume ratio of at least about 30 /mm.

The desired type of microstructure can be achieved by those of skill in the art by thermomechanically processing blocks of the titanium, utilizing a series of heating, quenching, and forging steps. For example, and in no way limiting of the invention, a working temperature is first determined. The working temperature is often in a range from about 700° C. to about 950° C. A rate of deformation and a degree of deformation are also determined. The working temperature, the rate of deformation, and the degree of deformation are determined by techniques known in the art. For example, these determinations can be made as set forth in PCT Application WO 98/17836 to Kaibyshev et al., the entire contents of which are fully incorporated by reference.

As disclosed in PCT Application WO 98/17836, several methods are disclosed for forming titanium, as embodied by the invention. For example, the titanium material that is subject to the inspection, as embodied by the invention, can be formed from nay one of the processes set forth in the Examples of the PCT Application WO 98/17836. Further, the titanium material that is subject to the inspection, as embodied by the invention, can be formed by other processes. For example, A method for preparing a titanium alloy article in which the titanium comprises a substantially controlled homogeneous fine grain microstructure. The method comprises the steps of: providing a titanium alloy article having an initial grain size (do); selecting a final homogeneous fine grain size (dk) to be achieved in the titanium alloy article; plotting a curve of the relationship between a recrystallized grain size (d) for the titanium alloy on the y-axis versus a strain temperature (T) for the alloy on the x-axis, between a range of 400° C. and a temperature of complete polymorphous transformation (Tcpt), in accordance with the relationship d=f(T); locating an area (T*) on the strain temperature axis to divide the temperature axis into two zones comprising a first zone 400° C. to T*, and a second zone T* to Tcpt, where the T* is located by first calculating a corresponding recrystallization grain size (d*) on the y-axis, where d* is logarithmically related to the initial grain size do; further locating, on the curve, the final grain size (dk) on the y-axis and then a corresponding strain temperature (Tk) on the x-axis; determining the heating and deforming step or steps to process the article based on Tk, where for Tcpt>Tk>T*, and there is at least one heat and deforming step to obtain the final grain size dk, where Tk<T*, there are at least two heat and deforming steps where each heat and deforming step occurs for a sufficient amount of time to reduce the grain size of the titanium alloy article until the final grain size dk is obtained; heating and deforming the titanium alloy article in accordance with the determined number of heat and deforming steps to achieve (dk), where each heat and deforming step has at least one heating and deforming step and one cooling step, where the heat and deforming step occurs for a sufficient period of time to reduce the grain size of the titanium alloy article, and where the deformation of the titanium alloy article is in a substantially controlled manner during each heat and deforming step at a rate of strain to achieve the desired grain size of the heat and deforming step, where the true strain during the deformation is greater than or equal to about 0.6 for each heat and deforming step, and where the subsequent cooling is controlled at a temperature below the heat and deforming step temperature at a cooling rate for substantially maintaining the reduced grain size obtained during the heat and deforming step; and repeating the step of heating and deforming the titanium alloy article in accordance with the determined number of heat and deforming steps to achieve homogeneous grain size(dk), until a final substantially controlled homogeneous grain size dk is obtained in the article having substantially homogeneous mechanical properties.

Another method for making a substantially controlled homogeneous fine grain microstructure in a titanium alloy article, as embodied by the invention, comprises the steps of: heating and deforming titanium material at a predetermined heat and deforming step temperature that is at or below a temperature of complete polymorphous transformation where the titanium alloy article has sufficient ductility and a starting grain size, in which the heat and deforming steps comprise at least one heat and deforming step and at least one cooling step. The heat and deforming steps is conducted for a sufficient amount of time to reduce the grain size from a starting grain size to a reduced grain size at the end of the heat and deforming step. The deforming of the titanium occurs in a controlled manner at a rate of strain that is able to achieve a desired grain size, where a true strain during the deformation is greater than or equal to about 0.6 for each heat and deforming step and where the cooling step is performed after the heat and deforming step at a temperature below the heat and deforming step temperature, in a controlled manner at a cooling rate to substantially maintain the reduced grain size obtained during the heat and deforming step. The method also includes continuing to heat and deform then cool the titanium alloy article, in which the heating occurs at lower heat and deforming step temperatures than the previous heat and deforming step temperature, so a reduction of grain size is achieved in subsequent heat and deforming steps until a final controlled grain size with controlled mechanical properties is obtained in the titanium alloy article.

Selection of process parameters are dependent, in part, on the particular titanium alloy being used, as well as the desired microstructure. The scope of the invention includes any known process for forming titanium with the grain structure, as embodied by the invention. The parameters are usually selected to promote the occurrence of dynamic recrystallization in the material, i.e., a phenomenon in which alloy grains being deformed rearrange themselves (recrystallizing) into finer grains with new crystallographic orientations. Dynamic recrystallization is known in the art and described, for example, by G. A. Salischev et al in "Formation of Submicrocrystalline Structure in the Titanium Alloy VT8 and its Influence on Mechanical Properties", Journal of Materials Science, 28 (1993), pp. 2898–2902, the contents of which are incorporated herein by reference. U.S. Pat. No. 5,399,212 (Chakrabarti et al) also provides some general instruction regarding the processing of titanium alloys, as does Forging and Properties of Aerospace Materials, The Metals Society, Book 188, Chameleon Press, London, 1978. The contents of both of these disclosures are incorporated herein by reference.

Additional treatment of the alloy, which is within the scope of the invention, may be undertaken after the microstructure has been achieved, to further enhance properties which may be desired for a given application, e.g., properties such as tensile strength, fracture toughness, and fatigue crack growth resistance. For example, thermal treatment steps may be carried out, such as solution treatment, stabilization (i.e., alpha/beta stabilization), and aging, with cooling steps usually occurring between the thermal steps. Those skilled in the art are familiar with the details of these steps. Flexibility in the selection of temperature cycles and other parameters is certainly allowable, as long as the desired microstructure is maintained.

This microstructure possesses yet another characteristic which is desired in the invention. As described in the examples which follow, the crystallographic orientation of the alpha grains is highly randomized. Substantially all of the alpha grains which surround any given alpha grain of a particular crystallographic orientation have a crystallographic orientation different from that of the given alpha grain, and different from that of substantially all of the other, surrounding alpha grains. Thus, the microstructure of the alloys for the present invention is characterized by the substantial absence of crystallographic grain alignment. Colonies of aligned grains are therefore generally absent from the microstructure. It is believed that the absence of these colonies decreases the level of "microstructural noise", thereby increasing the ability to inspect the alloys for defects, as further described in the examples.

The shape of the titanium alloy will depend on its intended use. Alloy shapes, as embodied by the invention, typically comprise a cross-sectional dimension (e.g., thickness or length) of at least about 1 inch, and a cross-sectional area of at least about 20 square inches. As one example, the alloys could be in the shape of plates having a thickness of about 1 inch or more.

The titanium alloy has a substantially cylindrical or substantially octagonal shape, or is in the shape of a rectangular prism. These shapes are often "billets" which result from the casting and/or hot-working of titanium-based ingots, as discussed previously. The cylindrical billets usually have a diameter of at least about 3 inches, and more often, a diameter of at least about 6 inches. Their length can vary widely, depending in part on the size of the ingot originally handled. Usually, the length is at least about 90 inches for titanium-based billets being processed into aerospace components. (Typically, the billets are eventually sectioned into smaller portions, e.g., smaller cylinders or discs. These sections can then be fabricated into desired parts, such as various turbine engine components.) Cylindrical billets, as well as the other alloy shapes described previously, can be readily treated as described above to provide the microstructural characteristics desired for the present invention. In fact, this invention provides for greatly-enhanced inspection of the billet itself by ultrasonic techniques, as described below.

Another embodiment, as embodied by the invention, relates to a method for improving the detectability of flaws in a titanium-based alloy being inspected with an ultrasonic device, comprising the step of thermomechanically processing the alloy to provide a microstructure which comprises an alpha phase, wherein (i) the average grain size of the alpha phase is substantially smaller than the cross-sectional area of the beam utilized in the examination; and (ii) the crystallographic orientation of the grains of the alpha phase is highly randomized.

Ultrasonic inspection techniques are known in the art and described, for example, in the Kirk-Othmer Encyclopedia of Chemical Technology, 3rd Edition, Vol. 16 (1981), pp. 65 et seq., and in many other references, such as the Foister et al article referenced above, and in the following articles: "Effects of Ti-6Al-4V Alloy Metallurgical Structures", F. R. Billman et al, Titanium Science and Technology, Plenum Press, 1973; and "The Influence of Microstructure on Ultrasonic Response in a Titanium Alloy Forging", B. Ginty et al, Titanium' 80 Science and Technology, edited by H. Kimura et al, 1980. Usually, the invention would be especially useful when immersion-type ultrasonic imaging systems are being employed. One example of such a device is described in U.S. Pat. No. 5,471,879 (Vinot et al), incorporated herein by reference.

An example of an ultrasonic system, as embodied by the invention, is a focused beam system. One such system relies on a multi-zone ultrasonic inspection apparatus and is described by R. Gilmore in U.S. Pat. No. 5,533,401 (incorporated herein by reference). Such a system provides a very uniform ultrasonic "interrogation" of the interior of a billet, in contrast to prior art inspection techniques used on billets having substantial thicknesses. Use of the multi-zone system for billets having microstructural characteristics provided by the present invention results in a much greater ability to detect any defects or irregularities in the material. Moreover, the multi-zone system (as well as the other ultrasonic inspection techniques) can efficiently be used to inspect the microstructure of the billet after it has been sectioned into smaller portions, or after the billet or smaller portions have been subjected to further thermomechanical processing techniques.

EXAMPLES

These examples are merely illustrative, and should not be construed to be any sort of limitation on the scope of the claimed invention. All parts are provided in weight percent, unless otherwise indicated.

Example 1

Two blocks of Ti-6242 (titanium, with 6% aluminum, 2% tin, 4% zirconium, and 2% molybdenum) were thermomechanically processed to achieve microstructural specifications according to the teachings of the present invention. The blocks had initial dimensions of 4 inches×4 inches×8 inches. After processing, the blocks had dimensions of 2.76 inches× 2.76 inches×5.9 inches. To examine the microstructure, two sections were taken through each block. One section (2.76 inches×2.76 inches) was a plane parallel to that defined by the short edges of the block. The other section was a plane (2.5 inches×2.76 inches) parallel to that defined by one short edge and the long edge of the block. Optical microscopy revealed that the grains were uniformly fine, and had a maximum diameter of about 5 microns. FIG. 1 illustrates the microstructure, which includes the equiaxed grains. As described below, the microstructure is substantially free of crystallographic texture. This is in contrast to the microstructure shown in FIG. 2, taken from a titanium-based alloy characteristic of the prior art.

The orientation of the grains was determined on a section of each block by electron back-scattered diffraction (EBSD), a well-known analytical technique. Those skilled in the art understand that the orientation of hexagonal crystal structures like those of titanium are typically expressed in terms of the direction in which the C-axis of the crystal is pointing. Quantitative comparisons of the orientation of two different titanium crystals can be made by measuring the vector dot product between their respective C-axis'.

Figure 3:
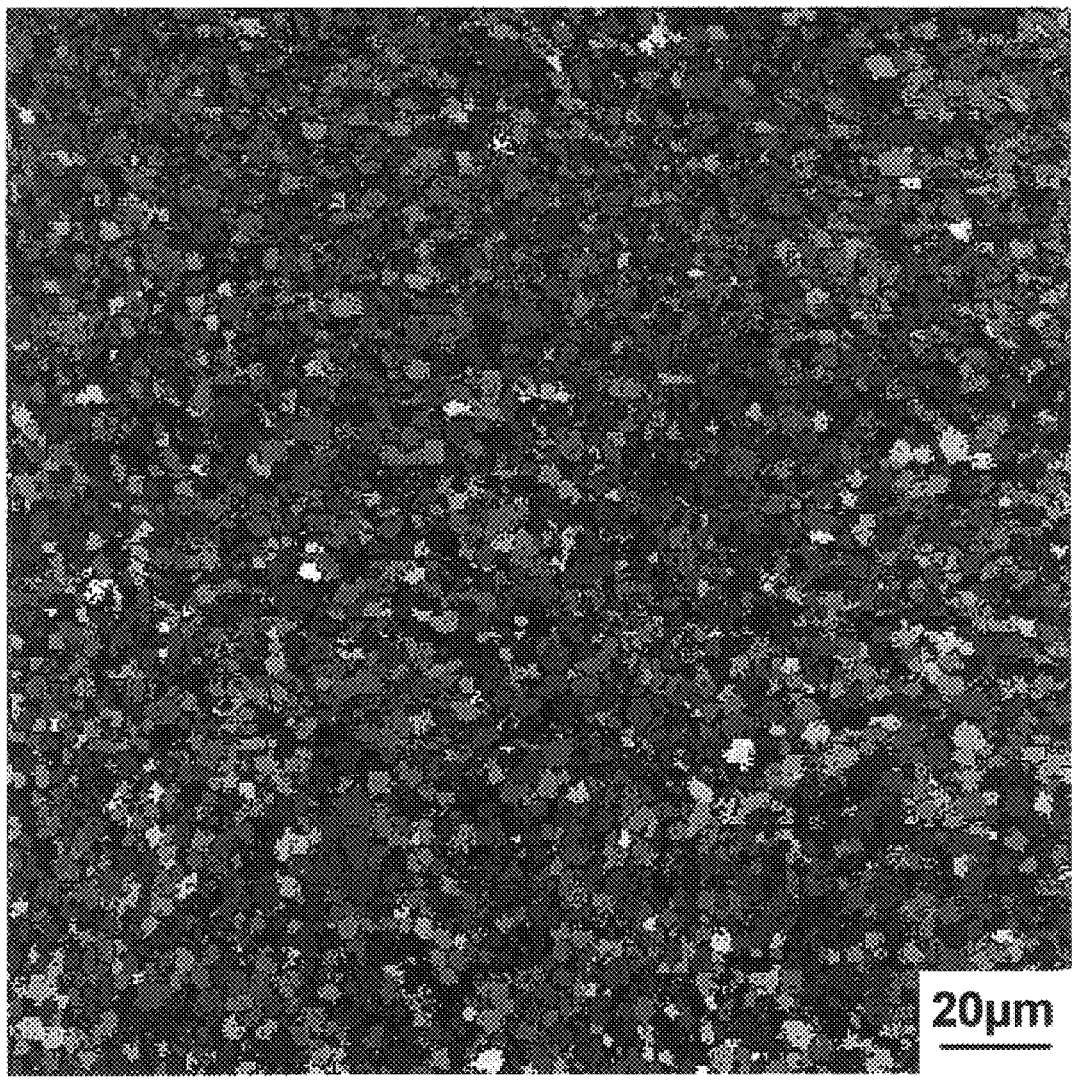
FIG. 3 is an orientation map of a titanium-based alloy for this invention, generated from an electron back-scattered diffraction apparatus.

The present examination showed regions of common texture being about 5 microns or less in diameter, while the neighboring regions had a random texture, as depicted in FIG. 3. Regions of the same shade of gray have [0001] ("basal") poles with the same inclination to the sample surface. The black-colored regions represent poles perpendicular to the sample surface, while white represents poles that lie in the plane of the sample surface. This map demonstrates that the small grains depicted in FIG. 1 are randomly oriented. Neighboring grains have different orientations (basal pole greater than 20 degrees away on average), demonstrating the absence of a colony structure.

Figure 2:
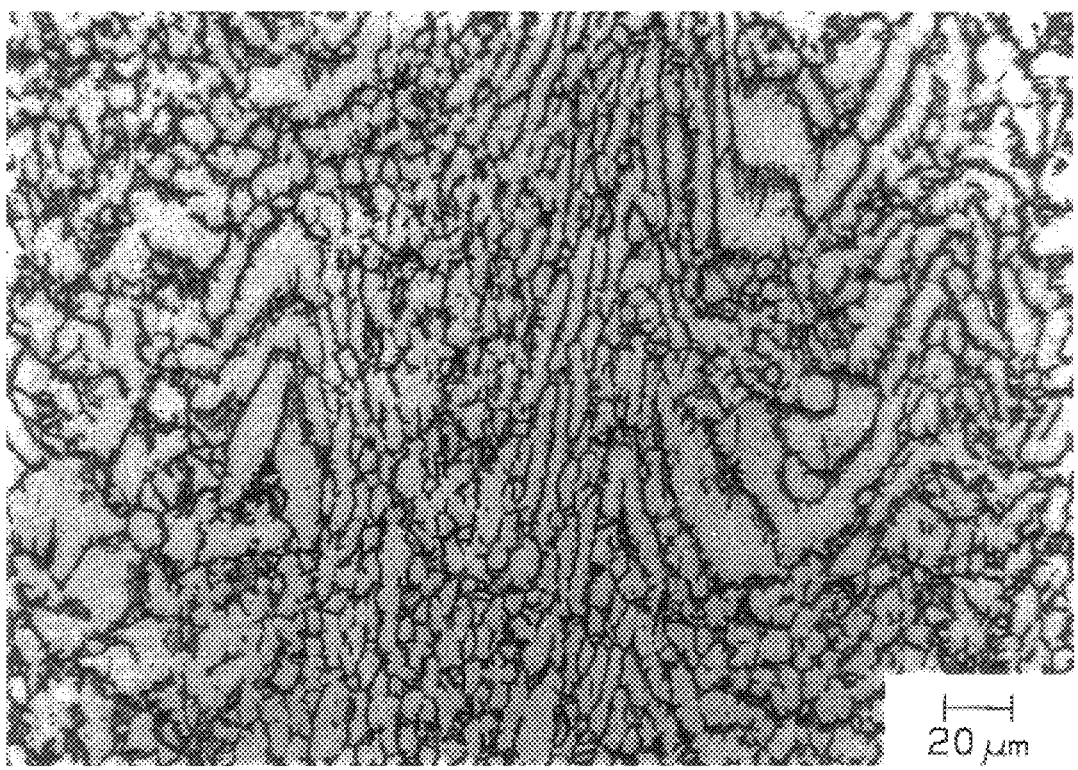
FIG. 2 is a photomicrograph of a titanium-based alloy which has a microstructure characteristic of the prior art.
Figure 4:
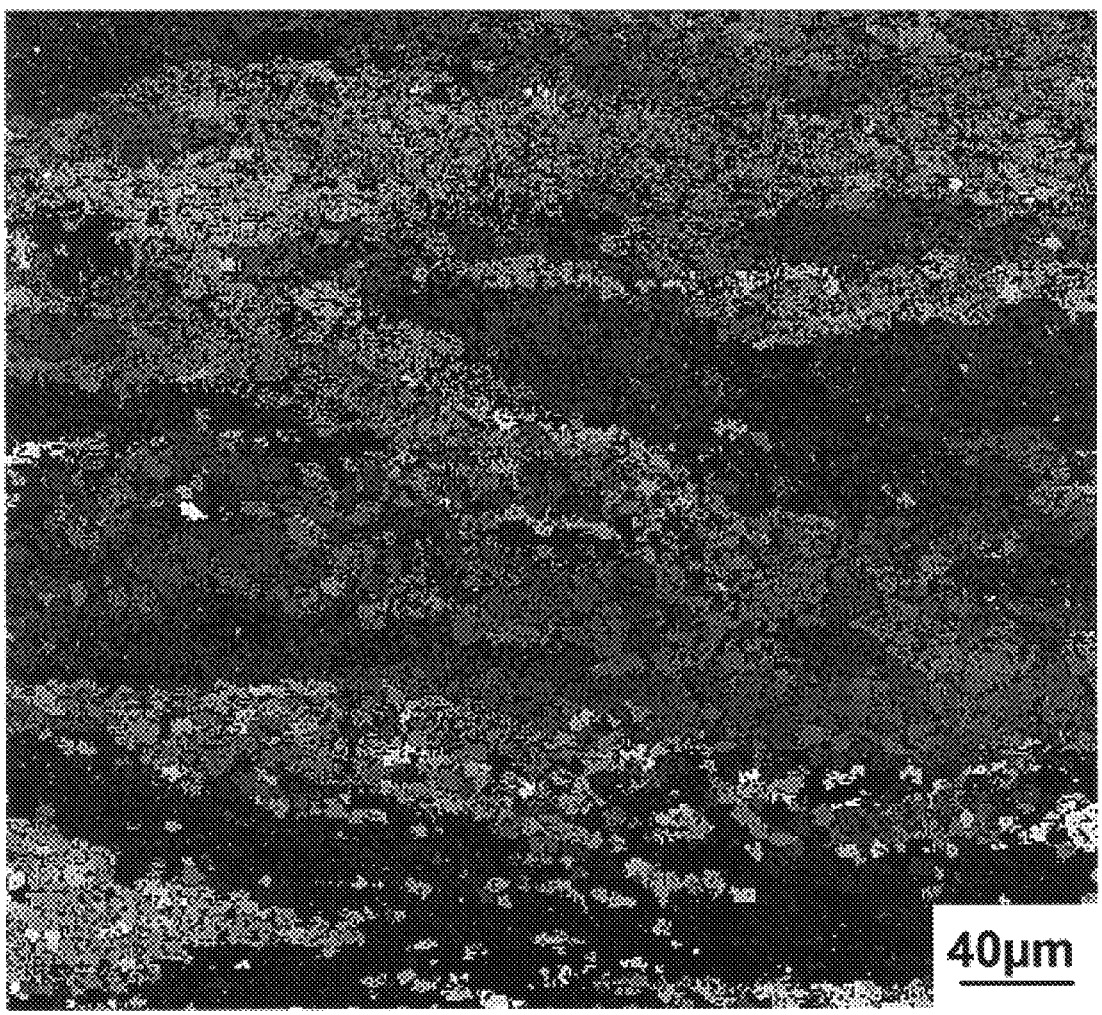
FIG. 4 is an orientation map of a titanium-based alloy of the prior art, generated from an electron back-scattered diffraction apparatus.

FIG. 4 is an orientation map of a titanium-based alloy of the prior art (FIG. 2), generated from the EBSD system. Regions of the same shade of gray have [0001] ("basal") poles with the same inclination to the sample surface. The colors black and white have the same significance as in FIG. 3. This map demonstrates that the grains of the material of FIG. 2 are located in "colonies" with similar orientations.

Figure 5:
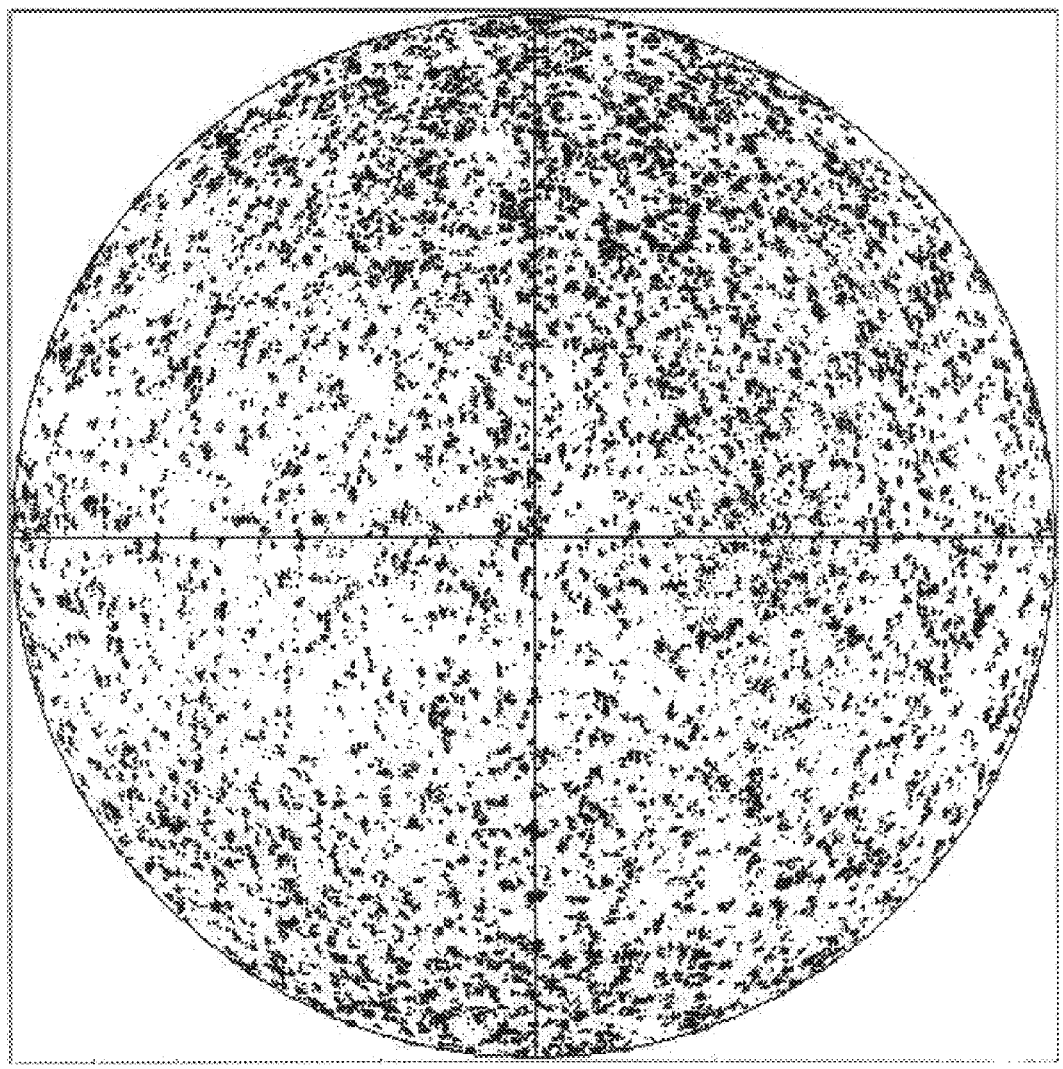
FIG. 5 is a pole figure based on the electron back-scattered diffraction data used in FIG. 3.

FIG. 5 is a [0001] pole figure based on the EBSD data used for FIG. 3. This figure effectively maps the orientation of grains within the examined portion of the alloy. The well-dispersed pattern of "dots", which represent the alpha grains, demonstrates the random presence of the grains, i.e., the random distribution of [0001] orientations for alloys of the present invention. The substantial absence of the undesirable colony structures in turn demonstrates the absence of crystallographic texture.

Figure 6:
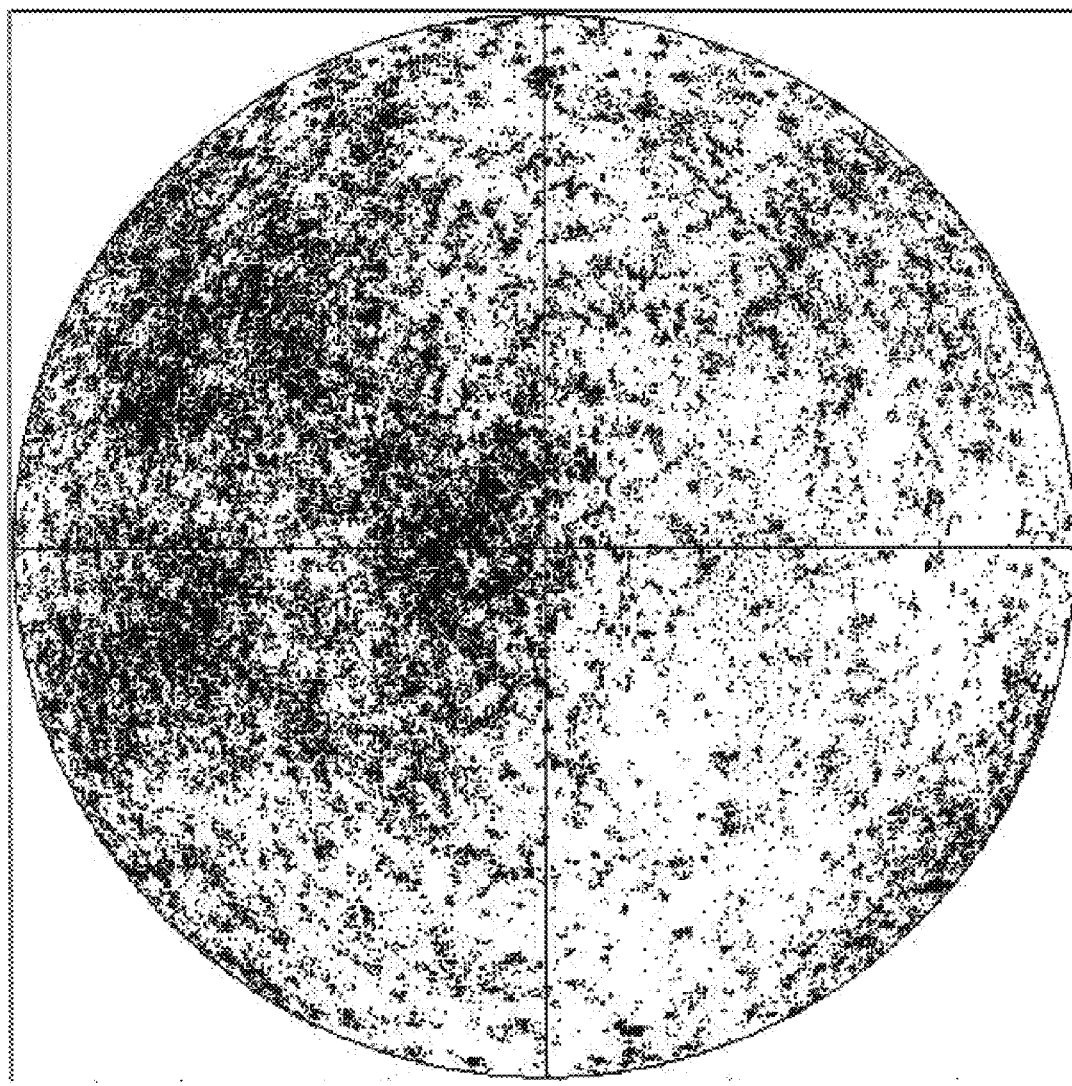
FIG. 6 is a pole figure based on the electron back-scattered diffraction data used in FIG. 4.

FIG. 6 is a [0001] pole figure based on the EBSD data used for FIG. 4. The figure clearly shows the non-homogenous distribution of [0001] orientations for the microstructure of a titanium-based alloy of the prior art.

Example 2

In this example, the comparative "inspectability" of blocks of titanium alloys was examined. Two blocks (samples 1 and 2, each having dimensions of 2.5 inches×2.5 inches×1.5 inches) were machined with 9 holes, 1/32 inch diameter (#2), with a flat bottom. The holes were drilled through one of the large faces, and were 0.5 inch deep. Sample 1 was machined from the Ti6242 material thermomechanically processed according to the present invention, as described in Example 1, while sample 2 (outside the scope of the present invention) was machined from the conventionally-processed billet material, using typical prior art techniques.

Ultrasonic C-scans were taken, using three transducers: 6.5 MHz f/4; 10 MHz f/7; and 20 MHz f/6. The blocks were scanned together, positioned side-by-side in a water tank. One scan at each frequency was taken at an attenuation which would not saturate the signal from any flat bottom hole. A second scan was taken at an attenuation pre-selected to nearly achieve saturation from the background microstructure.

Figure 7:
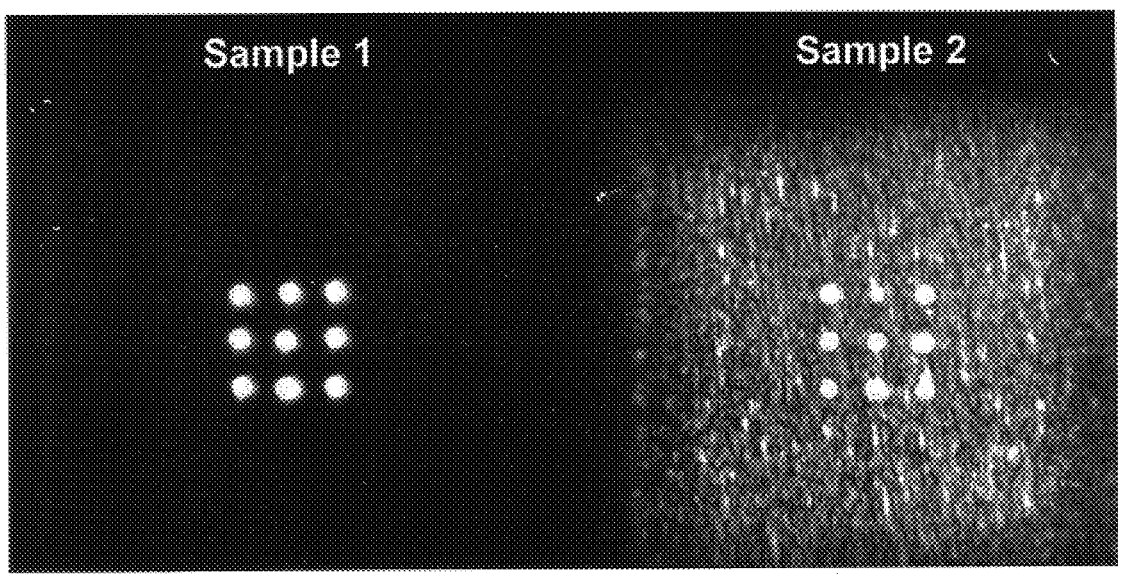
FIG. 7 is a depiction of ultrasonic C-scan data obtained for comparative titanium alloys.

FIG. 7 displays the C-scan results using the 6.5 MHz transducer, and an attenuation set to display the microstructural noise. The image of the C-scan data for a titanium-based alloy of the present invention is depicted on the left side of the figure, while the image of the C-scan data for a titanium-based alloy of the prior art is shown on the right side of the figure.

The signal for each flat bottom hole was taken as the average of the values of the 3×3 pixel array which contained the highest signal at its center pixel. Microstructural noise was measured at eight square regions on the block around the center array of flat bottom holes. Signal-to-noise values were determined according to the following relationship: (Signal−Average Noise)/(Maximum Noise−Average Noise). This provided a measurement of how "high" a signal stands above the noise. The results, tabulated in Table 1, demonstrate the improvement for the material processed according to the present invention.

TABLE 1

Comparative Signal-to-Noise (S/N) Quantities

| Transducer Type | Sample 1 S/N* | Sample 2** S/N* | Improvement (Ratio) |
|---|---|---|---|
| 6.5 MHz f/4 | 379.7 | 31.46 | 12:1 |
| 10 MHz f/7 | 333.7 | 31.23 | 10:1 |
| 20 MHz f/7 | 228.3 | 28.38 | 8:1 |

*For #2 Flat Bottom Holes
**Comparative Sample

Table 1 demonstrates, via a comparison of flat bottom hole blocks, an 8 to 12-fold improvement in signal-to-noise ratio for blocks prepared according to the present invention. Such an improvement represents a highly significant advance for the "inspectability" of titanium-based alloys. (The 6.5 MHz frequency is a typical transducer setting for current industry practice.)

While various embodiments are described herein, it will be appreciated from the specification that various combinations of elements, variations or improvements therein may be made by those skilled in the art, and are within the scope of the invention.

What is claimed is:

1. A titanium-based alloy having a microstructure that comprises a plurality of grains of an alpha phase, wherein the plurality of grains of the alpha phase has an average grain size of less than about 50 microns, the average grain size being substantially smaller than a cross-sectional area of an ultrasonic beam that is used to inspect the alloy; and wherein the plurality of grains of the alpha phase has a random distribution of crystallographic orientations and an absence of crystallographic texture.

2. The titanium-based alloy of claim 1, wherein the average grain size of the alpha phase is less than about 5 microns.

3. The alloy of claim 1, comprising an alpha phase and a beta phase.

4. The alloy of claim 1, comprising aluminum as an alloying element.

5. The alloy of claim 4, further comprising vanadium as an alloying element.

6. The alloy of claim 4, further comprising at least one element selected from the group consisting of tin, zirconium, and molybdenum as an alloying element.

7. The alloy of claim 1, having a composition (in approximate weight percent) selected from Ti-6 Al-4 V; Ti-6 Al-2 Sn-4 Zr-2 Mo; Ti-3 Al-2.5 V; Ti-6 Al-6 V-2 Sn; Ti-10 V-2 Fe-3 Al; Ti-5 Al-2.5 Sn; Ti-6 Al-2 Sn-4 Zr-6 Mo; Ti-4 Al-2 Sn-4 Mo-0.5 Si; Ti-5.5 Al-3.5 Sn-3 Zr-1 Nb-0.2 Mo-0.3 Si; Ti-5.8 Al-4 Sn-3.5 Zr-0.7 Nb-0.5 Mo-0.35 Si-0.06 C; Ti-5 Al-2 Sn-2 Zr-4 Cr-4 Mo; and Ti-6 Al-2.7 Sn-4 Zr-0.4 Mo-0.45 Si.

8. The alloy of claim 1, wherein the average grain size of the alpha phase is less than about 1% of the diameter of the ultrasonic beam utilized in an ultrasonic examination.

9. The alloy of claim 1, wherein the average grain size of the alpha phase is less than about 1% of the wavelength of a carrier frequency of the ultrasonic beam.

10. The alloy of claim 1, wherein the ultrasonic beam used to inspect the alloy comprises a focused beam.

11. The alloy of claim 1, wherein the microstructure comprises a texture in which substantially all of the alpha grains which surround any given alpha grain of a particular crystallographic orientation comprise a crystallographic orientation that is different from that of the given alpha grain, and different from that of substantially all of the other surrounding alpha grains.

12. A billet formed from a titanium-based alloy, the titanium-based alloy having a microstructure that comprises a plurality of grains of an alpha phase, wherein the plurality of grains of the alpha phase has an average grain size of less than about 50 microns, the average grain size being substantially smaller than a cross-sectional area of an ultrasonic beam that is used to inspect the alloy; and wherein the plurality of grains of the alpha phase has a random distribution of crystallographic orientations and an absence of crystallographic texture.

13. An article formed from a titanium-based alloy billet, the titanium-based alloy billet having a microstructure that comprises a plurality of grains of an alpha phase, wherein the plurality of grains of the alpha phase has an average grain size of less than about 50 microns, the average grain size being substantially smaller than a cross-sectional area of an ultrasonic beam that is used to inspect the alloy: and wherein the plurality of grains of the alpha phase has a random distribution of crystallographic orientations and an absence of crystallographic texture.

14. The article of claim 13, wherein the article comprises a cross-sectional dimension of at least about 1 inch, and a cross-sectional area of at least about 20 square inches.

15. The billet of claim 12, wherein the billet is a substantially cylindrical billet that comprises a diameter of at least about 3 inches.

16. The article of claim 13, wherein the average grain size of the plurality of grains of the alpha phase is less than about 5 microns.

17. The article of claim 13, wherein the titanium-based alloy comprises an alpha phase and a beta phase.

18. The article of claim 13, wherein the titanium-based alloy comprises aluminum as an alloying element.

19. The article of claim 18, wherein the titanium-based alloy further comprises vanadium as an alloying element.

20. The article of claim 18, wherein the titanium-based alloy further comprises at least one element selected from the group consisting of tin, zirconium, and molybdenum as an alloying element.

21. The article of claim 13, wherein the titanium-based alloy has a composition (in approximate weight percent) selected from Ti-6 Al-4 V; Ti-6 Al-2 Sn-4 Zr-2 Mo; Ti-3 Al-2.5 V; Ti-6 Al-6 V-2 Sn; Ti-10 V-2 Fe-3 Al; Ti-5 Al-2.5 Sn; Ti-6 Al-2 Sn-4 Zr-6 Mo; Ti-4 Al-2 Sn-4 Mo-0.5 Si; Ti-5.5 Al-3.5 Sn-3 Zr-i Nb-0.2 Mo-0.3 Si; Ti-5.8 Al-4 Sn-3.5 Zr-0.7 Nb-0.5 Mo-0.35 Si-0.06 C; Ti-5 Al-2 Sn-2 Zr-4 Cr-4 Mo; and Ti-6 Al-2.7 Sn-4 Zr-0.4 Mo-0.45 Si.

22. The article of claim 13, wherein the average grain size of the plurality of grains of the alpha phase is less than about 1% of the diameter of the ultrasonic beam utilized in the ultrasonic examination.

23. The article of claim 13, wherein the average grain size of the plurality of grains of the alpha phase is less than about 1% of the wavelength of a carrier frequency of the ultrasonic beam.

24. The article of claim 13, wherein the ultrasonic beam used to inspect the article comprises a focused beam.

25. The article of claim 13, wherein the article is a turbine engine component.

26. The article of claim 25, wherein the turbine engine component is a turbine disc.

27. A method for inspecting a titanium-based alloy to detect flaws in the titanium-based alloy, the titanium-based alloy comprising an alpha phase that is provided by thermomechanically processing the titanium-based alloy to provide a microstructure which comprises a plurality of grains of the alpha phase having an average grain size of less than 50 microns and a random distribution of crystallographic orientations and an absence of crystallographic texture, the method comprising:

ultrasonically inspecting the titanium-based alloy using an ultrasonic beam, the ultrasonic beam comprising a cross-sectional area that is greater than the average grain size of the plurality of grains of the alpha phase in the titanium-based alloy; and determining flaws based on the step of ultrasonic inspecting.

28. The method of claim 27, wherein the step of ultrasonically inspecting the titanium-based alloy comprises directing a multi-zone ultrasonic inspection apparatus at the titanium-based alloy.

29. The method of claim 27, wherein the average grain size of the alpha phase in the titanium-based alloy is less than about 5 microns.

30. The method of claim 27, wherein the titanium-based alloy further comprises at least one of a beta phase, and alloying elements selected from aluminum, vanadium, tin, zirconium, and molybdenum.

31. The method of claim 27, wherein the titanium-based alloy comprises a composition as an alloying element.

32. The method of claim 27, wherein the step of ultrasonically inspecting the titanium-based alloy comprises using an ultrasonic beam to inspect the titanium-based alloy wherein the average grain size of the plurality of grains of the alpha phase in the titanium-based alloy is less than about 1% of the cross-sectional area of the ultrasonic beam.

33. The method of claim 27, wherein the step of ultrasonically inspecting the titanium-based alloy comprises using an ultrasonic beam for inspecting the titanium-based alloy with a focused ultrasonic beam.

* * * * *